(12) United States Patent
Dumas et al.

(10) Patent No.: US 8,455,013 B2
(45) Date of Patent: Jun. 4, 2013

(54) USE OF AN EXTRACT OF COMMON MALLOW AS AN HYDRATING AGENT, AND COSMETIC COMPOSITION CONTAINING IT

(75) Inventors: Marc Dumas, Saint Jean Le Blanc (FR); Emmanuelle Noblesse, Donnery (FR); Valérie Krzych, Les Bordes (FR); Jean Hubert Cauchard, Orléans (FR)

(73) Assignee: LVMH Recherche, Saint Jean de Braye (FR)

( * ) Notice: Subject to any disclaimer, the term of this patent is extended or adjusted under 35 U.S.C. 154(b) by 85 days.

(21) Appl. No.: 12/500,824

(22) Filed: Jul. 10, 2009

(65) Prior Publication Data

US 2010/0098751 A1    Apr. 22, 2010

(30) Foreign Application Priority Data

Jul. 11, 2008 (FR) .................... 08 54780

(51) Int. Cl.
*A61K 36/00* (2006.01)
*A61K 9/56* (2006.01)
*A61K 9/60* (2006.01)
*A61K 9/14* (2006.01)

(52) U.S. Cl.
USPC ............ 424/725; 424/459; 424/774; 424/484

(58) Field of Classification Search
None
See application file for complete search history.

(56) References Cited

U.S. PATENT DOCUMENTS

| 5,166,139 A * | 11/1992 | Bombardelli et al. ........... 514/26 |
| 2006/0088616 A1* | 4/2006 | Seiberg et al. ................. 424/769 |
| 2007/0237847 A1* | 10/2007 | Henry et al. .................. 424/769 |

FOREIGN PATENT DOCUMENTS

| FR | 2801504 | 6/2001 |
| FR | 2814070 | 3/2002 |
| FR | 2818910 | 7/2002 |
| JP | 2006137690 | 6/2006 |
| KR | 2004046507 | 6/2004 |
| WO | WO 2007/007255 | 1/2007 |

OTHER PUBLICATIONS

Snyder "Classification of the Solvent Properties of Common Liquids," Journal of Chromatography A, May 22, 1974, 92, 2, 223-230.
Sougrat et al., "Functional Expression of AQP3 in Human Skin Epidermis and Reconstructed Epidermis", JID, Apr. 2002, 118(4), 678-685.
Verbavatz et al., "Expression of aquaporin 9 and 10 in human keratinocytes during differentiation, 5$^{th}$ International Conference on Aquaporins," Nara Japan, Jul. 2007, 1 page.
Search Report dated Feb. 16, 2009 in French Patent No. 0854780 filed Jul. 11, 2008.
Eggensperger, H. et al.; Pflanzenextrakt Mit Potential Die Schleimpolysaccharide Von Melva Silvestris Als Multiaktive Wirkstoffe Fuer Kosmetika; Parfumerie Und Kosmetik, Heuthig, Heidelberg, Germany, vol. 80, No. 7/08, Jan. 1, 1999, pp. 10-12, XP001173120.
Database WPI Week 200639, Thomson Scientific, London, GB; AN-2006-376199, XP002515294, Jun. 1, 2006, 3 pages.
Database WPI Week 200467, Thomson Scientific, London, GB; AN-2004-686013, XP002515295, Jun. 5, 2004, 1 page.

* cited by examiner

*Primary Examiner* — Chris R Tate
*Assistant Examiner* — Russell Fiebig
(74) *Attorney, Agent, or Firm* — Woodcock Washburn LLP

(57) ABSTRACT

The present invention relates to a novel use of an extract of common mallow for restoring, maintaining or reinforcing the state of moisturization of the skin; to a cosmetic composition containing it, and also to cosmetic care methods using said composition.

19 Claims, 2 Drawing Sheets

USE OF AN EXTRACT OF COMMON MALLOW AS AN HYDRATING AGENT, AND COSMETIC COMPOSITION CONTAINING IT

CROSS-REFERENCE TO RELATED APPLICATIONS

This application claims the benefit of French Patent Application No. 0854780, filed Jul. 11, 2008, the entirety of which is incorporated herein.

TECHNICAL FIELD

The present invention relates to a novel use of an extract of common mallow for restoring, maintaining or reinforcing the state of moisturization of the skin; to a cosmetic composition containing it, and also to cosmetic care methods using said composition.

BACKGROUND

Maintenance of skin moisturization is a major problem in the cosmetics industry, which is in search of moisturizing cosmetic agents that can be used in any type of cosmetic composition, and also new targets on which these active agents can act, especially to limit the evaporation of water or to improve the transportation of water in the epidermis.

Aquaporins (AQPs) are a family of transmembrane proteins which form channels that facilitate the diffusion of water and small molecules, such as glycerol and urea, in solution.

To date, 13 proteins of this family have been identified in man (numbered from AQP0 to AQP12). They are widely distributed in the body and most particularly in organs that are the site of considerable movement of water between different compartments, such as the kidneys (water reabsorption) or the skin (transepidermal water loss).

Certain aquaporins known as aquaglyceroporins, for instance AQP3 and AQP9, also show permeability to small solutes such as glycerol, urea, purines and pyrimidines, which also play an important role in maintaining the level of hydration of tissues.

AQP-3, revealed in the plasma membrane of human epidermal keratinocytes, is distributed throughout all live epidermis (R Sougrat et al. JID 2003, 118 : 678-685).

AQP9 has more recently been revealed in these same epidermal cells, but more locally in the upper (superficial) layers of the human epidermis (J M Verbavatz et al., *Expression of aquaporin 9 and 10 in human keratinocytes during differentiation*, 5th International Conference on Aquaporins, Nara Japan, July 2007).

This localization of AQP9 in the outermost layers of the skin, which are the ones that are the most exposed to dehydration, makes AQP9 a biological target of choice for improving the surface moisturization of the skin.

FR 2 801 504 discloses an extract of *Ajuga turkestanica* as an agent for stimulating the expression of AQP3 and its cosmetic use as a moisturizer.

WO 2007/007 255 discloses various agents for stimulating the expression of aquaporins AQP3 and AQP9 in the skin, and also their cosmetic use.

Common mallow (*Malva sylvestris*), also known as wild mallow or wood mallow, is a biennial herbaceous plant of the Malvacea family. The use of extracts of this plant in cosmetics is known.

FR 2 814 070 discloses a process for preparing an aqueous extract of leaves of the plant species *Malva sylvestris*, and the use of the said extract as an anti-ageing cosmetic agent in cosmetic compositions.

No document thus discloses the moisturizing properties of an extract of mallow (*Malva sylvestris*) via stimulation of the expression of AQP9 in epidermal cells.

This property makes the use of such an extract particularly advantageous in cosmetic compositions, for performing care via which it is sought to maintain or to promote the moisturization of the skin.

SUMMARY

The present invention is directed to methods for restoring, maintaining or reinforcing the state of moisturization of skin comprising applying to a part of the skin of a face or of a body, a cosmetic composition comprising an extract of common mallow (*Malva sylvestris*) in an amount effective for restoring, maintaining or reinforcing the state of moisturization of the skin.

Also within the scope of the invention are cosmetic compositions comprising, as one of the cosmetically active agents, a combination of an extract of common mallow (*Malva sylvestris*) and of at least one triterpenic saponin or a plant extract containing at least one triterpenic saponin.

The invention also encompasses methods of cosmetic care for restoring, maintaining or reinforcing the state of moisturization of skin, or for obtaining a preventive, lowering or retarding effect on the appearance of the signs of skin dryness. These methods comprise applying to a part of the skin of a face or of a body, a cosmetic composition comprising, as active agent, an extract of common mallow or a combination of an extract of common mallow and of at least one triterpenic saponin or a plant extract containing at least one triterpenic saponin, in an amount effective for restoring, maintaining or reinforcing the state of moisturization of the skin or in an amount efficient for obtaining a preventive, lowering or retarding effect on the appearance of the signs of skin dryness or both.

The invention also encompasses methods of cosmetic care for facilitating the refatting of dry skin in order to improve the skin-barrier effect with respect to evaporation of water contained in the superficial layers of the epidermis. These methods comprise applying to a part of the skin of a face or of a body, a cosmetic composition comprising, as active agent, an extract of common mallow or a combination of an extract of common mallow and of at least one triterpenic saponin or a plant extract containing at least one triterpenic saponin, in an amount effective for facilitating the refatting of dry skin.

DETAILED DESCRIPTION OF ILLUSTRATIVE EMBODIMENTS

Figure 1:
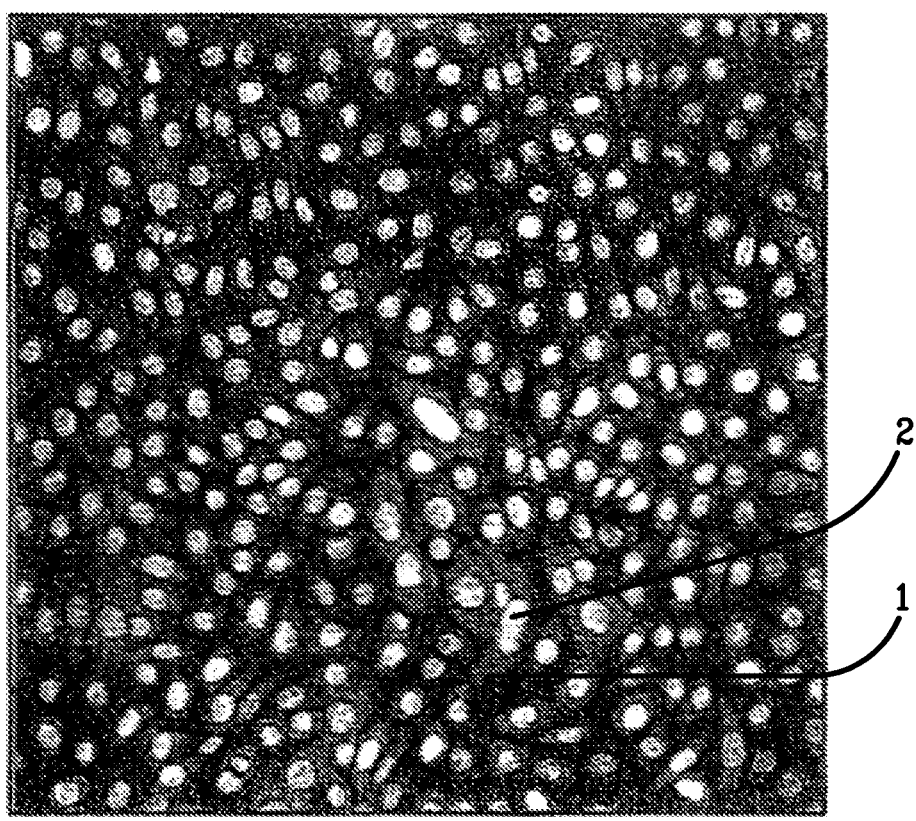
FIG. 1 is an image to be analysed according to the methods of the invention described herein in the context of immuno-labelling allowing the detection of cell nuclei and of the expression of AQP9.

The inventors of the present invention have now discovered that the expression of AQP9 in human epidermal keratinocytes is strongly stimulated by an extract of common mallow.

An aim of the invention is to provide a novel skin moisturizer, especially for restoring, maintaining or reinforcing the state of moisturization of the skin.

Another aim of the invention is to provide a cosmetic composition comprising such a moisturizer.

An aim of the present invention is also to provide a cosmetic care method using the said cosmetic composition, especially for restoring, maintaining or reinforcing the state of moisturization of the skin.

Finally, an aim of the present invention is to provide a simple solution that can be used on an industrial and cosmetic scale.

According to a first aspect, the invention thus relates to the use in a cosmetic composition of an extract of common mallow (*Malva sylvestris*) as a moisturizer for restoring, maintaining or reinforcing the state of moisturization of the skin. Thus, the invention is also directed towards the use of an extract of common mallow (*Malva sylvestris*) as a moisturizer for restoring, maintaining or reinforcing the state of moisturization of the skin.

The extract according to the invention is preferably an extract of common mallow (*Malva sylvestris*) leaves, more particularly obtained by treating the leaves of the said plant with a polar solvent or a mixture of polar solvents.

According to the present invention, the term "polar solvent" means that the solvent has a polarity index value P' that is greater than or equal to 4. The polarity index is a magnitude calculated on the basis of thermodynamic magnitudes (of solubility and of change of state) that reveals the more or less polar nature of a molecule. Reference will be made, for the polarity indices of solvents, to the article by L. R. Snyder (*J. Chromatogr.*, 92 (1974), 223-230), which is included in the present patent application by reference.

The polar solvent, or the polar solvents forming a mixture, is (are) chosen from water, a $C_1$-$C_4$ alcohol, especially ethanol or butanol, or alternatively a glycol, especially glycerol, butylene glycol or propylene glycol.

The preferred extract of common mallow is more particularly obtained using water or an aqueous-alcoholic mixture such as a mixture of water and ethanol.

According to one particular embodiment of the invention, the extract of common mallow is an aqueous extract, such as the product sold by the company Silab under the trade name VITACTYL CLAIR®.

According to the invention, the extract of common mallow as defined previously is present as active agent in a cosmetic composition, in an amount that is effective for obtaining the desired effect during a topical application.

The term "effective amount" means an amount of the extract of common mallow that makes it possible to obtain the desired effect, in the present case action on moisturizing the skin.

According to another aspect of the invention, the tests performed by the inventors have shown that the moisturizing effect produced by the extract of common mallow may be significantly improved when said extract is combined with at least one triterpenic saponin.

Specifically, a particularly significant synergistic effect on the expression of AQP9 is observed in epidermal cells treated with a combination of an extract of common mallow and of at least one triterpenic saponin.

Triterpenic saponins, also known, without preference, as triterpenic saponosides, are compounds formed from a sugar and a triterpene group whose backbone is formed from six isoprene units, i.e. 30 carbon atoms. These compounds are very frequently found, in very varied structures, in many plant species such as *Rhaponticum carthamoides, Aralia mandshurica, Bacopa monniera, Bryonia alba, Eleutherococcus senticosus, Panax ginseng, Gynostemma pentaphyllum, Codonopsis pilosula, Tinospora cordifolia, Withania somnifera, Tribulus terrestris, Dioscorea, Smilax excelsa, Paris polyphylla, Cornus florida, Yucca, Smilax aristolochiaefolia, Asparagus officinalis, Hedera helix, Trigonella fenug raecum, Centella asiatica. Glycine max (soja), Phaseolus vulgaris, Phaseolus aureus, Phaseolus lunatus, Vicia faba, Lens culinaris, Cicer arietum, Vigna angularis, Vigna mungo, Oxytropis ochrocephala, Oxytropis glabra, Pisum sativum, Sophora favescens, Asparalus membranaceus, Crotalaria albida, Arachis hypogea, Galega officinalis, Wistaria brachybotrys, Trifolium repens*, or alternatively a plant of the genus *Medicago*, in particular *Medicago alfalfa* and *Medicago sativa* (alfalfa).

These triterpenic saponins are found in particular in tissues rich in nutrient substances, such as roots, tubers, leaves, flowers and seeds.

These tissues rich in nutrient substances constitute a plant material of choice for performing a process of extraction of said triterpenic saponins they contain, for the purpose of preparing a plant extract containing them, optionally followed by a step directed towards purifying and isolating these compounds.

Thus, a second subject of the invention relates to the use in a cosmetic composition of a combination of an extract of common mallow (*Malva sylvestris*) and of at least one triterpenic saponin or of a plant extract containing it, as a moisturizer for restoring, maintaining or reinforcing the state of moisturization of the skin.

The mallow extract of the combination is preferably as defined previously.

A preferred triterpenic saponin is one of those present in the plant species *Centella asiatica*, especially asiaticoside of formula (I):

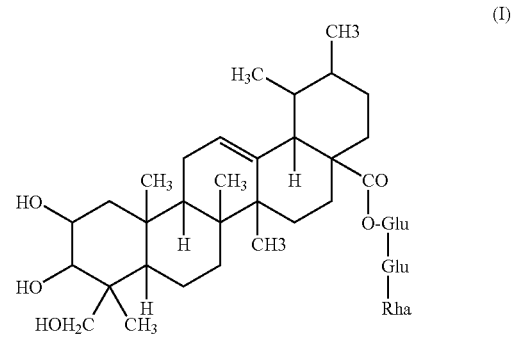

madecassoside of formula (II)

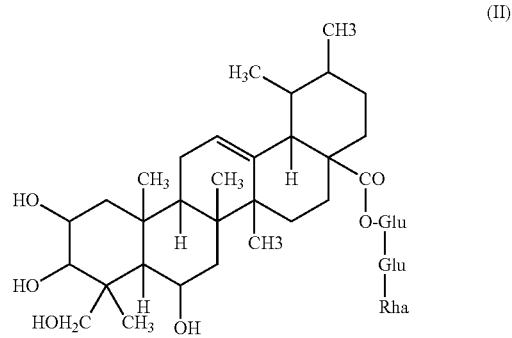

According to the invention, a first preferred combination is thus that in which the triterpenic saponin is asiaticoside, madecassoside, or mixtures thereof, in isolated form or in the form of a plant extract containing the same.

The combination that is more particularly preferred is that of an extract of mallow as defined previously and of an extract of *Centella asiatica* containing at least one triterpenic saponin.

According to this embodiment of the invention, the extract of *Centella asiatica* is obtained by treating leaves of the said plant with a polar solvent or a mixture of polar solvents, which may be the same as the one used for producing the extract of common mallow.

The polar solvent or the polar solvents forming a mixture is (are) then advantageously chosen from water, a $C_1$-$C_4$ alcohol, especially ethanol or butanol, or alternatively a glycol, especially glycerol, butylene glycol or propylene glycol.

According to a third aspect, the invention relates to a cosmetic composition characterized in that it comprises, as active agent, a combination of an extract of common mallow (*Malva sylvestris*) and of at least one triterpenic saponin or an extract containing it.

According to one preferred embodiment, the cosmetic composition comprises, as active agent, a combination of an extract of *Malva sylvestris* leaves and an extract of *Centella asiatica* leaves, each extract being as described previously and more particularly obtained using a polar solvent or a mixture of polar solvents.

According to one particular embodiment of the invention, the cosmetic composition comprises from 0.0001% to 1% and preferably from 0.01% to 0.1% by weight of dry extract of *Malva sylvestris*, and from 0.0001% to 0.5% by weight of dry extract and preferably from 0.01% to 0.1% by weight of dry extract of *Centella asiatica*.

The weight ratio A/B of dry extract of *Malva sylvestris* (A) and of *Centella asiatica* (B), respectively, in the cosmetic composition according to the invention is between 1/10 and 500/1, preferably between 1/5 and 50/1 and more particularly preferably between 1/2 and 20/1.

According to one embodiment variant of the invention, the moisturizer may be at least partially encapsulated in vectors, preferably in unilamellar or multilamellar liposomes.

Inclusion of the active agent in such a vector facilitates the diffusion of said moisturizer through the stratum corneum to reach the deeper layers of the epidermis in order thus to exert their moisturizing effect therein.

The moisturizer thus encapsulated may be advantageously stabilized by being included in a cosmetic composition of aqueous gel type, or alternatively stabilized with an alginate in the case of a cosmetic composition of oil-in-water emulsion type.

The cosmetic composition according to the invention may also comprise one or more other molecules or plant extracts that have moisturizing properties, such as glycols, in particular glycerol, or natural polyols, natural or synthetic ceramides, urea, hyaluronic acid, or alternatively an extract of *Ajuga turkestanica*, an extract of *Vanda coerulea*, retinoic acid or D-xylose.

These molecules or extracts, which also have a skin-moisturizing effect according to a mechanism different from stimulation of the expression of AQP9, may thus play a role complementary to that of the active agents of the invention.

Among the other cosmetic agents that may also be used in the composition according to the invention, mention may be made more particularly of agents for stimulating the epidermal kallikreins, which regulate desquamation at the surface of the skin, in particular an extract of nopal, agents for stimulating the synthesis of epidermal lipids that play an essential role in the water-barrier effect of the stratum corneum and the smoothness of the skin, in particular an extract of seeds of *Helianthus annuus* L. or of *Luffa cylindrica*, agents that stimulate the terminal differentiation of keratinocytes or transglutaminase, to reinforce the formation of corneocytes and the skin barrier, especially β-ecdysone or calcium derivatives such as calcium gluconate or calcium pyrrolidonecarboxylate, or alternatively active agents that stimulate epidermal renewal, in particular wheatgerm oil, agents that promote the formation of tight junctions and thus limit intercellular water losses, in particular an extract of *Castanea sativa* or *Sanchi saponins*, cosmetic agents against bags and dark rings under the eyes, in particular ascorbyl glucoside or hesperetin, agents for stimulating epidermal glycosaminoglycan (GAG) synthesis, such as D-xylose or a xylose derivative, especially a C-glycoside such as C-β-D-xylopyranoside-n-propan-2-one, C-β-D-(3,4,5-triacetoxy)-xylopyranoside-n-propan-2-one or C-β-D-xylopyranoside-2-hydroxy-propan-2-one, and derivatives thereof.

Besides at least one active agent, the cosmetic composition also comprises at least one cosmetically acceptable excipient that is useful for preparing said composition.

The composition may in particular comprise a solvent, or a mixture of solvents, used for dissolving or dispersing the plant extract(s) used as moisturizer. This solvent or this mixture of solvents may be identical to or different from that used for the extraction.

The cosmetic composition according to the invention may be in the form of a serum, a lotion, an emulsion, a cream, a hydrogel, preferably a mask, or alternatively a stick or a patch.

Finally, according to a fourth aspect, a subject of the invention is a cosmetic care method, characterized in that it comprises the application, to at least one concerned area of facial or bodily skin, of a cosmetic composition comprising as active agent an extract of common mallow or a combination of said extract and of at least one triterpenic saponin or a plant extract containing it, to restore, maintain or reinforce the state of moisturization of the skin and/or to obtain a preventive, lowering or retarding effect on the appearance of the signs of skin dryness.

According to one particular embodiment, stimulation of the expression of AQP9 in the epidermis improves the diffusion of glycerol, which allows the esterification of fatty acids to mono-, di- and then triglycerides, which are essential constituents of the intercorneocytic lipids at the surface of the skin.

The said cosmetic care method is thus also directed towards facilitating the refatting of dry skin to improve the barrier effect of the skin with respect to evaporation of the water contained in the superficial layers of the epidermis.

Other aims, characteristics and advantages of the invention will emerge clearly from the explanatory description that follows, which is made with reference to several examples of implementation of the invention that are given purely as illustrations and shall not in any way limit the scope of the invention. In the examples, the temperature is in degrees Celsius, the pressure is atmospheric pressure and the amounts or percentages are given on a weight basis, unless otherwise indicated.

EXAMPLES

Materials and Method

The study is performed on normal human keratinocytes (NHK) isolated from surgical residues of mammary or abdominal operations. The NHKs are isolated from samples of human skin treated with thermolysin to isolate the epidermis thereof.

1. Cell Culture

The NHKs isolated from samples of human skin are cultured in T75 flasks in whole KSFM medium (Invitrogen Gibco, 17005-034) at 37° C. and 5% $CO_2$ up to subconfluence, and are then trypsinized and frozen at P1 in cryotubes at −196° C.

After thawing, the NHKs are cultured by passage 1 in whole KSFM medium in a T75 flask. At the preconfluence stage, the NHKs are treated with trypsin and inoculated at a rate of 20 000 cells per well in Lab-Tek II 8-well culture systems (Nalge Nunc International). 4 wells per treatment condition.

2. Treatment

After culturing for 24 hours, the cells are treated with the various active agents tested.

Active Agents Tested:

Extract of *Malva sylvestris* leaves sold under the name Vitactyl Clair® by the company Silab, France. This extract is in the form of an aqueous solution containing 2.1 w/w % solids.

Extract of *Centella asiatica* leaves (INCI: *Centella asiatica* leaf extract) in powder form (*Centella asiatica* heterosides, Bayer HealthCare). The triterpenic saponin (asiaticoside and madecassoside) content of the extract is greater than 70% by weight.

Preparation of the Treatment Solutions:

50 mg of powdered extract of *Centella asiatica* are dissolved in 500 µL of DMSO (stock solution, 100 mg/ml). 100 µL of the stock solution are then diluted in 10 ml of KSFM (1 mg/mL solution).

Separately, the commercial solution of extract of common mallow (Vitactyl Clair®) is diluted in the KSFM medium to obtain the treatment solutions below at 0.5 v/v % and 1 v/v % of the starting commercial solution, corresponding, respectively, to 105 µg of dry extract and 210 µg of dry extract per ml of treatment solution.

Treatments:

The concentrations of the extract solutions are expressed as weight of dry extract/ml of KSFM medium:
- control (KSFM medium)
- DMSO control (KSFM medium+DMSO 1/1000)
- extract of *Malva sylvestris* 105 µg/ml (0.5%)
- extract of *Malva sylvestris* 210 µg/ml (1%)
- extract of *Centella asiatica* 11 µg/ml
- extract of *Centella asiatica* 33 µg/ml
- extract of *M. sylvestris* 105 µg/ml+extract of *C. asiatica* 11 µg/ml
- extract of *M. sylvestris* 105 µg/ml+extract of *C. asiatica* 33 µg/ml
- extract of *M. sylvestris* 210 µg/ml+extract of *C. asiatica* 11 µg/ml
- extract of *M. sylvestris* 210 µg/ml+extract of *C. asiatica* 33 µg/ml The cells are treated at about 50% of confluence for 48 hours. After the treatment, the cells will have reached the confluence stage.

3. Immunolabelling

After 48 hours of treatment, the KSFM is aspirated. The cells are rinsed with PBS (PBS tablets, Invitrogen Gibco) and then fixed onto slides using formalin (buffered neutral 10% formalin solution, Sigma) for 10 minutes. After rinsing with PBS, the culture chambers are filled with a 0.1% Triton solution (Triton X-100, Sigma) for 10 minutes, and then rinsed twice with PBS.

According to a first step, the cells are first covered with a solution of PBS/1% BSA (BSA, Sigma) for 30 minutes at room temperature. The PBS/BSA solution is then removed from the slides.

According to a second step, the cells are then covered with a primary anti-AQP9 antibody solution (goat polyclonal sc-14989) diluted 100-fold, for 60 minutes at room temperature. The slides are rinsed with a PBS solution.

According to a third step, the cells are finally covered with a secondary anti-goat antibody solution diluted 200-fold (Alexa Fluor 546, rabbit anti-goat IgG, Molecular Probes). The cell nuclei are stained with Sytox green (Molecular Probes) at 20 000-fold dilution in the secondary antibody solution. The slides are incubated for 60 minutes in the absence of light and at room temperature, and are then rinsed with PBS.

4. Mounting

The slide culture chamber is dismantled and a few drops of mounting medium (Fluorescent Mounting Medium, DAKO) are placed on the cells are then covered with a 24×60 mm slide.

The slides are stored at 4° C. in the dark.

5. Acquisition of the Photographs by Confocal Microscopy

Photographs are taken by confocal microscopy (Zeiss Axioplan microscope, and BioRad krypton-argon laser) using the LaserSharp 2000 software (BioRad).

For each condition, four photographs are taken in red fluorescence (AQP9 expression) and in green fluorescence (cell nuclei) according to the same acquisition parameters (gain, iris) with a ×20 objective lens. The images are then combined to form a composite image.

6. Image Analysis

The photographs are analysed using the Leica QWin image analysis software. A program is created in order to quantify the AQP9 expression relative to the number of cells.

The analysis is performed in several steps:

Step 1: Opening of the Image to be Analysed (FIG. 1)

The image resulting from the combination of the original photographs shows the labelling of AQP9 (1), in red, and the labelling of the cell nuclei (2), in green.

Step 2: Detection of the AQP9 Labelling

The image analysis software detects the positive pixels for the labelling of AQP9. The measurement will be performed on the number of red pixels detected, which corresponds to the amount of AQP9 present in each cell.

Step 3: Detection of the Cell Nuclei

The software detects the green pixels corresponding to the cell nuclei. The measurement will be performed on the number of objects.

Step 4: Determination of the Measurement Area

The measurement area is formed by the entire microscopic field shown in the attached FIG. 1.

Step 5: Displaying the Results
- area represented by the AQP9 labelling
- number of cell nuclei=number of cells
- area measured

7. Statistical Analysis

The statistical analysis consists of a calculation of the mean, of the standard deviation and of the confidence interval ($\alpha$=0.05) of the following parameters:

expression of AQP9 per cell (area of AQP9/number of cells)

number of cells per field, representative of the cell proliferation

Example 1

Activity of an Extract of *Malva sylvestris*

Figure 2:
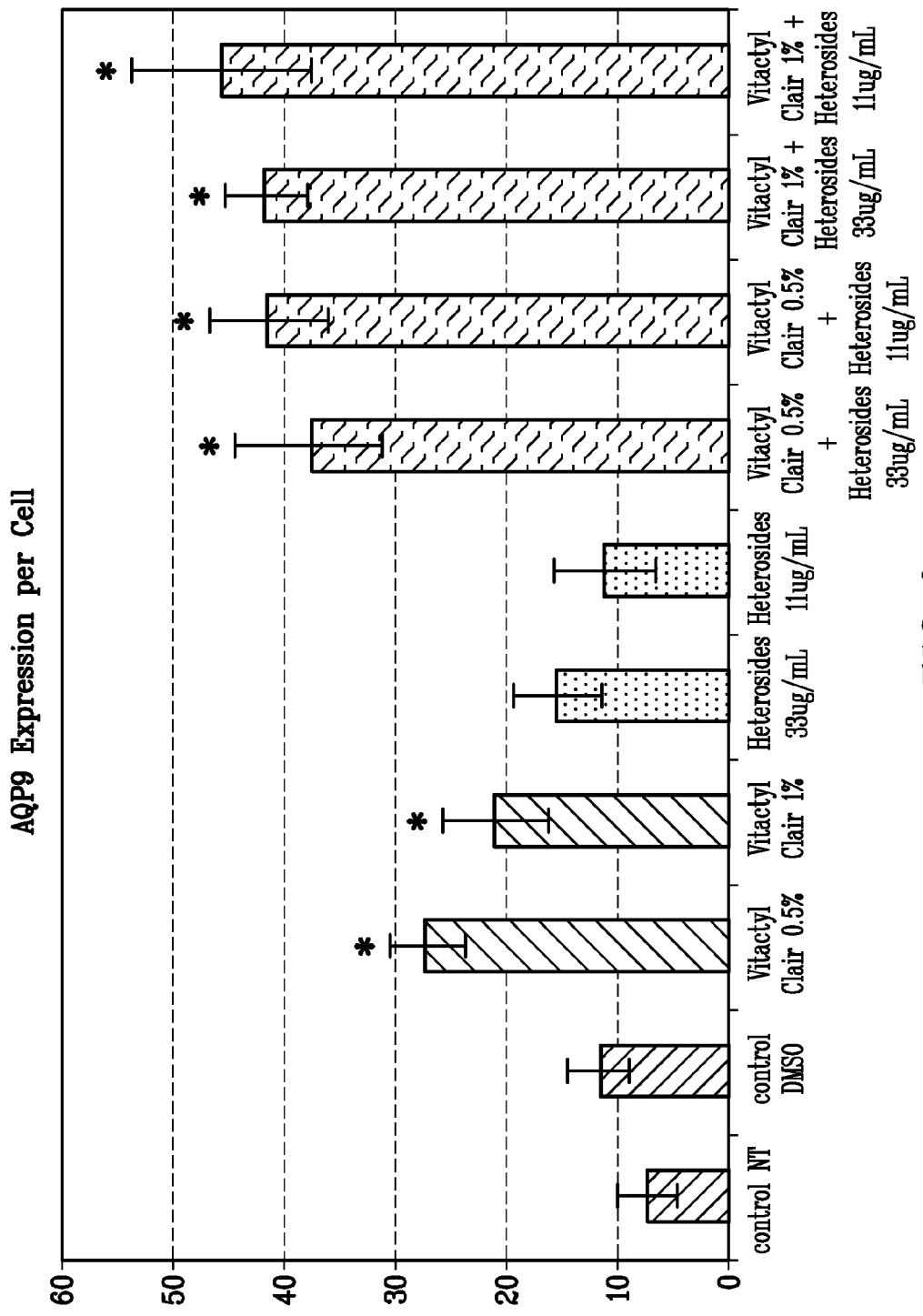
FIG. 2 shows the expression of AQP9 per cell, measured according to the methods of the invention described herein.

Table I below discloses the results for the treatment with each of the test solutions. This table is reproduced in the form of histograms in FIG. 2.

The expression of AQP9 is normalized in order to be expressed as an area of AQP9 expressed per cell, the cell number being determined by counting the number of nuclei in the sample observed.

TABLE I

| Treatment | Expression of AQP9/cell Mean (standard deviation) | Test |
|---|---|---|
| Control NT | 7.18 (2.79) | |
| Control solvent (DMSO) | 11.5 (2.72) | |
| Extract of *C. asiatica* 11 μg/ml | 11.0 (4.62) | NS |
| Extract of *C. asiatica* 33 μg/ml | 15.1 (4.00) | NS |
| Extract of mallow 105 μg/ml | 27.1 (3.46) | S |
| Extract of mallow 210 μg/ml | 21.0 (4.90) | S |
| Extract of mallow 105 μg/ml + extract of *C. asiatica* 11 μg/ml | 41.5 (5.44) | S |
| Extract of mallow 105 μg/ml + extract of *C. asiatica* 33 μg/ml | 37.7 (6.96) | S |
| Extract of mallow 210 μg/ml + extract of *C. asiatica* 11 μg/ml | 45.7 (8.18) | S |
| Extract of mallow 210 μg/ml + extract of *C. asiatica* 33 μg/ml | 41.7 (3.86) | S |

Conclusion

The extract of *Malva sylvestris* significantly stimulates the expression of AQP9 in the epidermal cells. The combination of the extracts of *Malva sylvestris* and of *Centella asiatica* has a synergistic effect as regards the expression of AQP9.

Example 2

Moisturizing Fluid Comprising an Extract of Common Mallow Leaves

The extract of common mallow (*Malva sylvestris*) leaves is an aqueous solution containing 2.1 w/w % of dry extract (Vitactyl Clair®, Silab).

The percentages are indicated on a weight basis relative to the weight of the final composition.

| | % |
|---|---|
| Aqueous solution of extract of *Malva sylvestris* | 1.0 |
| Phenoxyethanol | 0.9 |
| Acrylates/$C_{10-30}$ alkyl acrylate crosspolymer (Pemulen TR-1) | 0.5 |
| Steareth-2 (Brij 72 flakes) | 1.2 |
| Steareth-21 (Brij 721 P) | 1.1 |
| Isononyl isononanoate | 7.4 |
| Stearyl alcohol | 0.3 |
| 95% cetyl alcohol | 0.3 |
| Dimethicone 100 CS | 0.3 |
| Powdered tetrasodium EDTA | 0.2 |
| Tocopheryl acetate | 0.2 |
| Sodium hydroxide | <0.1 |
| Fragrances | <0.1 |
| Purified water | qs 100 |

This composition is an oil-in-water emulsion, which may be applied to facial skin every day to obtain the desired moisturizing effect.

Example 3

Moisturizing Cream Comprising an Extract of Common Mallow

The mallow extract solution is identical to that used in Example 2.

The extract of *Centella asiatica* is in the form of a powder, sold under the name *Centella asiatica* heterosides. This powder is dissolved in water to a minimum of 3 w/w %, in order to be used in the composition of the example.

The percentages are indicated on a weight basis relative to the weight of the final composition.

| | % |
|---|---|
| Extract of *Centella asiatica* | 0.1 |
| Aqueous solution of extract of *Malva sylvestris* 1.2 w/w % | 1.0 |
| Phenoxyethanol | 0.7 |
| Acrylates/$C_{10-30}$ alkyl acrylate crosspolymer | 0.3 |
| Ammonium acryloyldimethyltaurate/vp copolymer (Aristoflex AVC) | 0.4 |
| Steareth-2 | 1.0 |
| Steareth-21 | 0.9 |
| Isononyl isononanoate | 6.2 |
| Stearyl alcohol | 0.5 |
| 95% cetyl alcohol | 0.5 |
| Glyceryl tricaprate/caprylate | 2.2 |
| Powdered tetrasodium EDTA | 0.2 |
| Tocopheryl acetate | 0.2 |
| Fragrances | 0.2 |
| Sodium hydroxide | <0.1 |
| Purified water | qs 100 |

This composition is an oil-in-water emulsion, which is applied daily to facial skin to obtain the desired moisturizing effect.

Example 4

Serum Comprising a Combination of an Extract of Common Mallow and an Extract of *Centella asiatica* as Moisturizer The solution of extract of mallow and the extract of *Centella asiatica* are in accordance with Example 2.

| | % |
|---|---|
| Solution of extract of *Malva sylvestris* 1.2 w/w % | 1.0 |
| Extract of *Centella asiatica* | 0.1 |
| Plant glycerol | 5.0 |
| Disodium EDTA dihydrate | 0.1 |

-continued

|  | % |
|---|---|
| Phenoxyethanol | 0.5 |
| Sclerotium gum (Amigel) | 1.0 |
| Acrylates/C$_{10-30}$ alkyl acrylate crosspolymer | 0.2 |
| Starch aluminium octenylsuccinate (Dry Flo Plus) | 2.0 |
| 1,3-Butylene glycol | 3.0 |
| Polysorbate 20 (Tween20) | 1.0 |
| Tocopheryl acetate | 0.2 |
| Sodium hydroxide | <0.1 |
| Fragrances | <0.1 |
| Purified water | qs 100 |

This composition is an aqueous solution that can be applied daily to facial skin to obtain the desired moisturizing effect.

What is claimed:

1. A cosmetic composition comprising from 0.001% to 5% of an extract of common mallow (*Malva sylvestris*), by weight of the composition, in combination with from 0.0001% to 0.1% of at least one triterpenic saponin or a plant extract containing at least one triterpenic saponin, by weight of the composition.

2. The cosmetic composition according to claim 1, wherein the extract of common mallow is an extract of common mallow leaves and the triterpenic saponin is asiaticoside, madecassoside, a mixture thereof, or a plant extract containing the same.

3. The cosmetic composition according to claim 1, wherein the plant extract containing at least one triterpenic saponin is an extract of *Centella asiatica*.

4. The cosmetic composition according to claim 3, comprising from 0.001% to 5% by weight of an extract of common mallow and from 0.0001% to 0.1% by weight of the extract of *Centella asiatica*.

5. The cosmetic composition according to claim 3, wherein the weight ratio of dry extract of the extract of common mallow and of the extract of *Centella asiatica* is between 1/10 and 500/1.

6. The cosmetic composition according to claim 1, wherein said combination is at least partially encapsulated in unilamellar or multilamellar liposomes.

7. The cosmetic composition according to claim 1, further comprising one or more agents or plant extracts that have moisturizing properties selected from the group consisting of glycols, glycerol, natural polyols, natural or synthetic ceramides, urea, hyaluronic acid, an extract of *Ajuga turkestanica*, an extract of *Vanda coerulea* and retinoic acid.

8. The cosmetic composition according to claim 1, further comprising one or more other cosmetic agents selected from the group consisting of an extract of nopal, an extract of seeds of *Helianthus annuus* L., an extract of seeds of of *Luffa cylindrica*, beta-ecdysone, calcium gluconate, calcium pyrrolidonecarboxylate, wheatgerm oil, an extract of *Castanea sativa*, an extract of *Sanchi saponins*, ascorbyl glucoside, hesperetin, D-xylose, a xylose derivative, a C-glycoside, C-β-D-xylopyranoside-n-propan-2-one, C-β-D-(3,4,5-triacetoxy)xylopyranoside-n-propan-2-one, C-β-D-xylo-pyranoside-2-hydroxy-propan-2-one, and derivatives thereof.

9. The cosmetic composition according to claim 1, comprising at least one cosmetically acceptable excipient and wherein the cosmetic composition is in the form of a serum, a lotion, an emulsion, a cream, a hydrogel, preferably a mask, a stick or a patch.

10. The cosmetic composition according to claim 1, wherein the combination of the extract of common mallow (*Malva sylvestris*) and the at least one triterpenic saponin is effective to increase the amount of AQP9 protein in the skin.

11. A method for restoring, maintaining or reinforcing the state of moisturization of the skin, comprising
applying, to a part of the skin of the face or of the body in need thereof, the cosmetic composition according to claim 1.

12. The method according to claim 11, wherein said extract is an extract of common mallow leaves.

13. The method according to claim 11, wherein said extract is obtained by treating leaves of said plant with a polar solvent or a mixture of polar solvents.

14. The method according to claim 13, wherein said polar solvent, or said polar solvents forming a mixture, is chosen from water, a $C_1$-$C_4$ alcohol or a glycol.

15. The method according to claim 13, wherein said extract is obtained using water or an aqueous-alcoholic mixture.

16. The method according to claim 11, wherein the triterpenic saponin is asiaticoside, madecassoside, a mixture thereof, or a plant extract containing the same.

17. Method according to claim 16, wherein said plant extract is an extract of *Centella asiatica* leaves obtained by extracting the leaves with a polar solvent or a mixture of polar solvents.

18. A method of cosmetic care selected from the group consisting of
a method for restoring, maintaining, or reinforcing the state of moisturization of the skin, and
a method for obtaining a lowering or retarding effect on the appearance of the signs of skin dryness,
comprising
applying to a part of the skin of the face or of the body in need thereof, of the cosmetic composition according to claim 1.

19. A method of cosmetic care for facilitating the refatting of dry skin to improve the skin-barrier effect with respect to evaporation of water contained in the superficial layers of the epidermis, comprising
applying to a part of the skin of the face or of the body in need thereof, of the cosmetic composition according to claim 1.

* * * * *